US00PP18462P2

(12) United States Plant Patent
Blokland

(10) Patent No.: US PP18,462 P2
(45) Date of Patent: Jan. 29, 2008

(54) ***ASTILBE* PLANT NAMED 'WHITE SENSATION'**

(50) Latin Name: ***Astilbe simplicifolia* hybrid**
Varietal Denomination: White Sensation

(76) Inventor: Rob Blokland, De Hoef Oostzijde 117a, De Hoef (NL), 1426 AJ ( * ) Notice: Subject to any disclaimer, the term of this patent is extended or adjusted under 35 U.S.C. 154(b) by 25 days.

(21) Appl. No.: 11/515,543

(22) Filed: Sep. 5, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Penny J. Aguirre

(57) ABSTRACT

A new cultivar of *Astilbe simplicifolia* hybrid named 'White Sensation' that is characterized by its pure white flowers borne on upright to cascading panicles over very dark green foliage and combined with a compact plant habit.

2 Drawing Sheets

Botanical classification: *Astilbe simplicifolia* hybrid.
Varietal denomination: 'White Sensation'.

BACKGROUND OF THE INVENTION

The present invention relates to a new and distinct cultivar of *Astilbe simplicifolia* and will be referred to hereafter by its cultivar name, 'White Sensation'. 'White Sensation' represents a new *Astilbe,* an herbaceous perennial grown for landscape use.

The inventor discovered the new cultivar, 'White Sensation', as a chance seedling that arose in a cultivated area in Noorden, The Netherlands in the summer of 1993. Although the parentage is unknown, the characteristics of the new cultivar and the presence of the cultivars *Astilbe simplicifolia* hybrid 'Sprite' (not patented) and *Astilbe japonica* hybrid 'Ellie' (not patented) in the area suggest that they are likely parents.

The new cultivar 'White Sensation' was selected as unique for having the plant habit of 'Sprite' combined with dark colored foliage and white flowers.

Asexual reproduction of the new cultivar was first accomplished by taking divisions in De Hoef, The Netherlands in 1995. It has been determined that the characteristics of the new cultivar are stable and are reproduced true to type in successive generations.

SUMMARY OF THE INVENTION

The following traits have been repeatedly observed and represent the characteristics of the new cultivar after observing plants grown outdoors in a field and in containers for two years in De Hoef, The Netherlands. These attributes in combination distinguish 'White Sensation' from all other varieties of *Astilbe* known to the inventor.

1. 'White Sensation' exhibits dark green foliage
2. 'White Sensation' exhibits white flowers presented on upright to arched panicles.
3. The plant habit of 'White Sensation' is clump-forming, broadly upright, and compact.
4. 'White Sensation' is cold hardy at least to U.S.D.A. Zones 5.

'White Sensation' is most closely related to the likely parents, *Astilbe simplicifolia* hybrid 'Sprite' and *Astilbe japonica* hybrid 'Ellie'. White sensation is similar to 'Sprite' in plant habit, but differs in having white flowers rather than light pink flowers and in having darker green foliage. 'White Sensation' is similar to 'Ellie' in having pure white flowers, however 'White Sensation' differs in having a more compact plant habit and darker colored foliage. 'White Sensation' can also be compared to the white flowered *Astilbe* 'Snowdrift' (not patented), however it is an *Astilbe×arendsii* hybrid and has lighter, medium green colored foliage.

BRIEF DESCRIPTION OF THE PHOTOGRAPHS

The plants and plant parts in the photographs depict a two-year old plant of 'White Sensation' as grown outdoors in a 20 cm container in De Hoef, The Netherlands.

The photograph on the first sheet provides an overall view of the new *Astilbe* in bloom.

The photograph on the top of the second sheet is a close-up view of the flowers of 'White Sensation' and the photograph on the bottom of the second sheet is a close-up view of a leaf of 'White Sensation'.

The colors in the photographs are as close as possible with the photographic and printing technology utilized. The color values cited in the detailed botanical description accurately describe the colors of the new *Astilbe.*

DETAILED BOTANICAL DESCRIPTION

The following is a detailed description of two year-old plants of the new cultivar as grown outdoors in 20 cm containers in De Hoef, The Netherlands for 2 years with average day temperatures ranging from 14° C. to 35° C. and average night temperatures ranging from 10° C. to 18° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'White Sensation' is an *Astilbe simplicifolia* hybrid.

Parentage: Naturally occurring chance seedling of *Astilbe simplicifolia* hybrid, parentage is unknown with *Astilbe simplicifolia* hybrids 'Sprite' and 'Ellie' as likely parents.

General description:

*Blooming period.*—Begins in mid July and continues for about 6 weeks.

*Plant type.*—Herbaceous perennial.

*Plant habit.*—Clump-forming, dwarf, compact, and broadly upright.

*Height and spread.*—Average of 46 cm in height, 50 cm in spread.

*Hardiness.*—Known to be hardy at least to U.S.D.A. Zone 5, colder zones have not been tested.

*Culture.*—Prefers humus-rich, moist but well-drained soils in partial shade or full sun in areas where summers are cool with sufficient moisture.

*Diseases and pests.*—No unique susceptibility or resistance to diseases or pests has been observed.

*Root description.*—Fine, wiry, dark colored and freely branched.

Growth and propagation:

*Propagation.*—Stem division.

*Cropping time.*—Roots fully develop in 22 cm pot in about 20 weeks from a one eye stem division.

*Growth rate.*—Moderate growth rate.

Stem description (flowering stems):

*Stem color.*—Young and mature stems; 144A with 187A to 187B near base.

*Stem size.*—Average of 28.6 cm in length and 2 mm in diameter.

*Stem quantity.*—Average of 10 per 22 cm container.

*Stem surface.*—Slightly glossy and pubescent with a sparse covering of soft hairs about 2 mm in length and N167B in color.

*Stem aspect.*—Strong, mostly held upright.

*Branching habit.*—No lateral branches, flowering stems emerge from a basal rosette of foliage.

Foliage description:

*Leaf division.*—Bi-ternate.

*Leaf attachment.*—Petiolate.

*Leaf arrangement.*—Alternate.

*Leaf number.*—Average of 3 per flowering stem and an average of 3 basal leaves per stem.

*Internode length.*—Average of 7.6 cm.

*Leaf size.*—Average of 14.6 cm in length and 17.3 cm in width.

*Leaflet quantity.*—Average of 21 per leaf.

*Leaflet shape.*—Terminals; narrow ovate to narrow elliptic, laterals; narrow ovate.

*Leaflet base.*—Attenuate.

*Leaflet apex.*—Acute.

*Leaflet venation.*—Pinnate, not conspicuous, color on upper lower surface 148B, color on lower surface 148A.

*Leaflet margins.*—Biserrate.

*Leaflet size.*—Lateral leaflets; average of 2.4 cm in length and 1.1 cm in width, terminal leaflets; average of 3.2 cm in length and 2.2 cm in width.

*Leaflet surface.*—Upper surface; slightly rugose, lower surface; sparsely pubescent with short strigose hairs an average of 1 mm in length and 157A to 157D in color (especially prevelant on main viens), glossy, rough to touch.

*Leaflet color.*—Young foliage upper surface; 143A, young foliage lower surface; 143C to 144A, mature foliage upper surface; darker than 137A, mature foliage lower surface; 137B to 137C.

*Petioles.*—144A in color with base of 187B, average of 1 mm in diameter and 8.3 cm in length, surface is glabrous.

*Petiolules.*—144A in color with base of 187B, average of 1 mm in diameter and 2.3 cm in length, surface is glabrous.

Flower description:

*Inflorescence type.*—Numerous single rotate shaped flowers arranged on pyramidal panicles.

*Inflorescence aspect.*—Upright and cascading.

*Inflorescence size.*—Average of 17.4 cm in height and 15.5 cm in width.

*Flower fragrance.*—Faint, sweet.

*Flower quantity.*—Average of 750 per inflorescence, approximately 7,500 flowers per plant.

*Flower lastingness.*—Average of 10 days per flower, panicles blooms for about 6 weeks, flowers persistent.

*Flower buds.*—Ovate in shape, average of 1.5 mm in diameter and 2 mm in length, 157D in color and 145A near base.

*Flower aspect.*—Upright, outward, and drooping.

*Flower shape.*—Rotate.

*Flower size.*—About 4 mm in depth and 8 mm in diameter.

*Petals.*—Average of 5, separate, narrow obovate in shape, margin is entire, apex is obtuse, upper and lower surface is glabrous and dull, color of upper and lower surface (opening and mature) is pure white and whiter than any R.H.S. colour chart, color fades to 175A, average of 5 mm in length and 1 mm in width.

*Calyx.*—Campanulate, sepals fused at base, average of 3 mm in length and 4 mm in diameter.

*Sepals.*—5, ovate in shape, margin is entire, apex is obtuse, base is cuneate and fused, surface is smooth and dull, color of upper and lower surface when immature; 145C, color of upper and lower surface when mature; pure white (whiter than R.H.S. colour chart) with a base of 155D, about 1 mm in width and 1.5 mm in length.

*Bracts.*—2, lanceolate in shape, 144B in color, unequal with one about 1 mm in width and 3 mm in length and the other about 0.75 mm in width and 1.5 mm in length, attenuate apex, base fused to rachis, color between 155B and 145D with upper portion 71A.

*Peduncles.*—Average of 17.1 cm in length and 1.5 mm in width, held upright, strong, color 144A to 144B and 157D towards apex, glabrous surface.

*Pedicels.*—About 0.75 mm in length and 0.5 mm in width and 157D in color, glabrous surface.

Reproductive organs:

*Gynoecium.*—2 Pistils, club-shaped, about 1.8 mm in length, stigma N155A in color and minute, style is about 1.7 mm in length and N155A in color, ovary is superior and N155A in color.

*Androcoecium.*—About 10 stamens, anthers are broadly ovate in shape, basifixed, about 0.2 mm in length and width and N155A in color, filaments are about 1.8 mm in length and 71C in color, pollen is low in quantity and 158D in color.

*Seed.*—No seed development has been observed.

It is claimed:

1. A new and distinct cultivar of *Astilbe* plant named 'White Sensation' as herein illustrated and described.

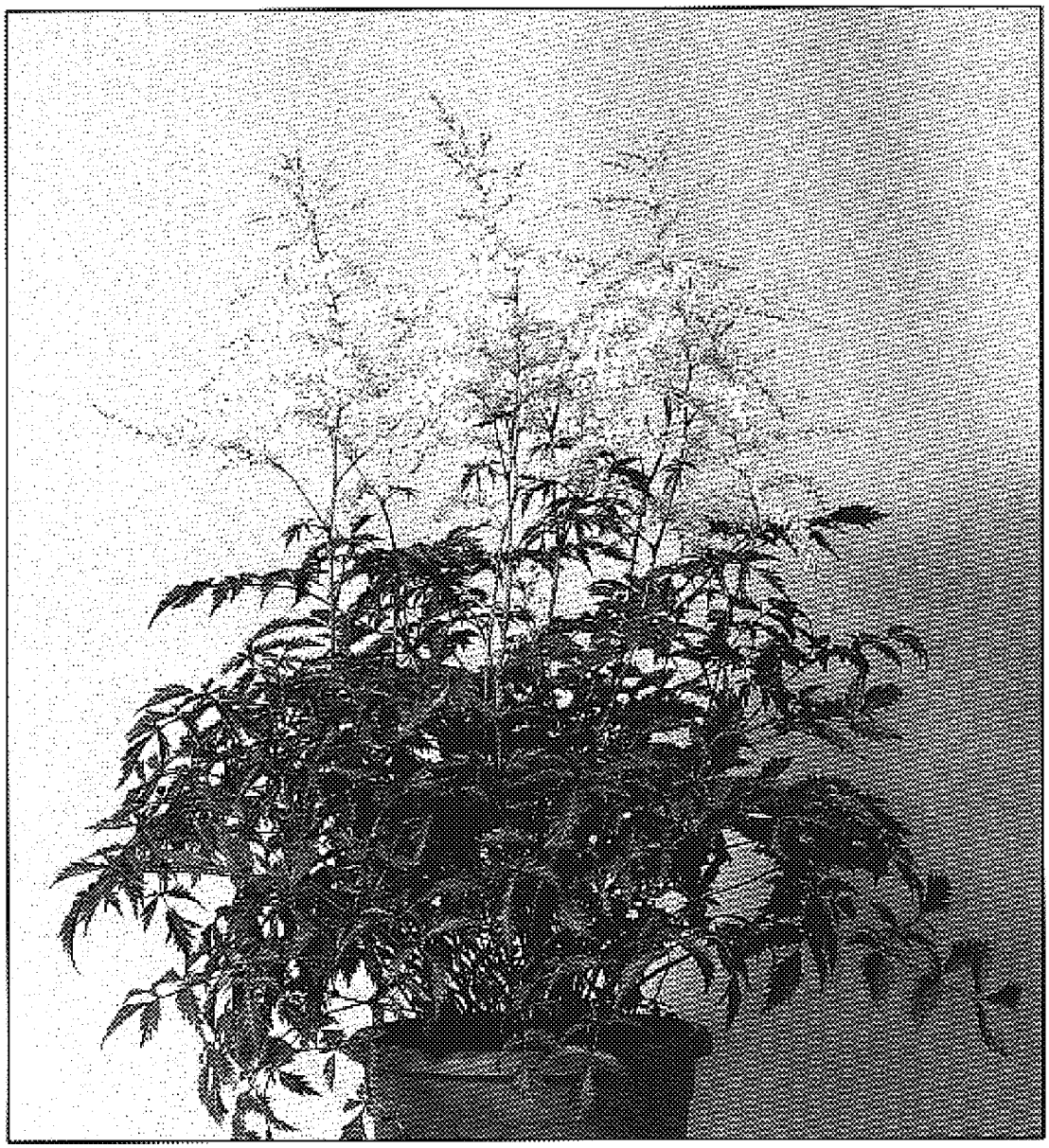

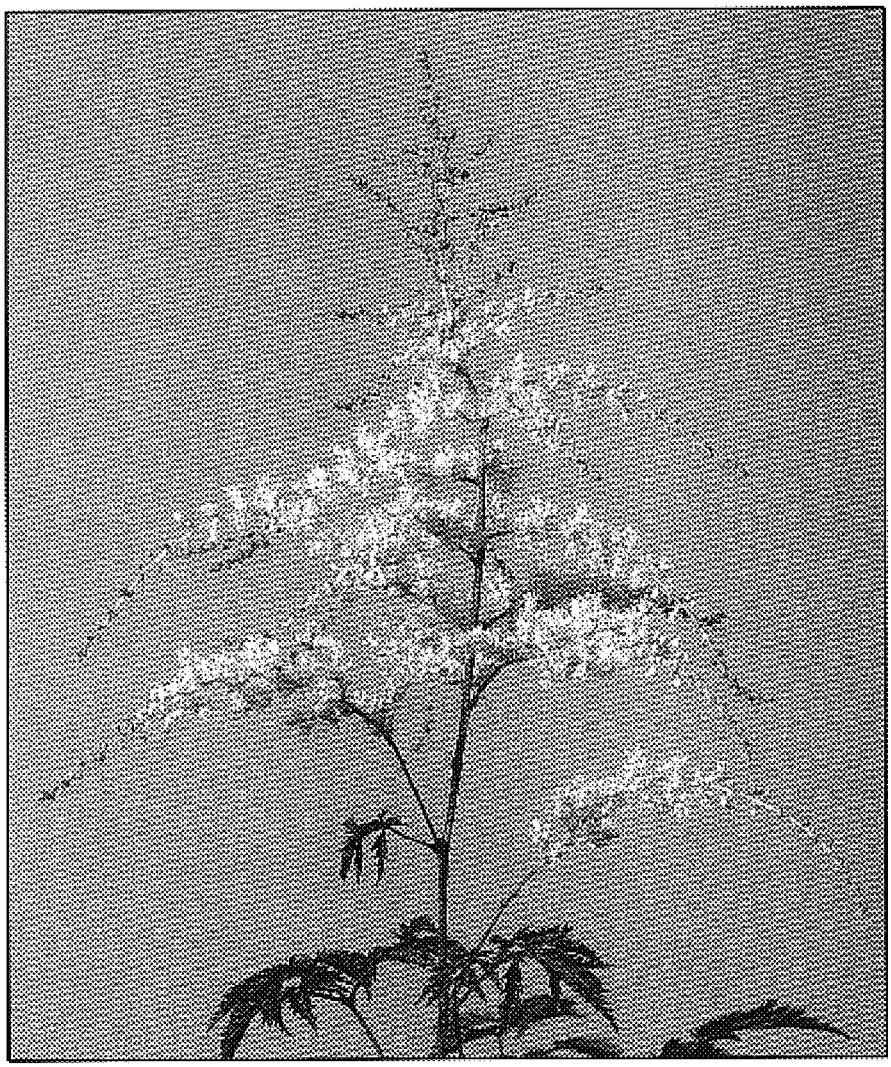
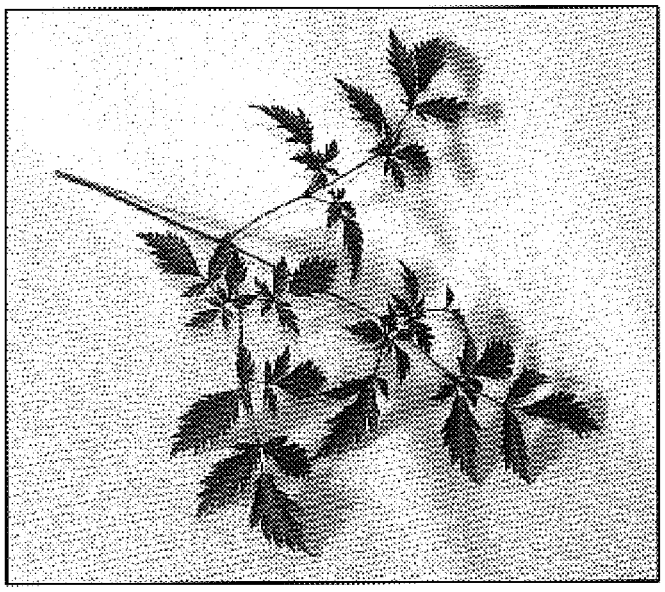

* * * * *